US006319898B1

(12) United States Patent
Davies et al.

(10) Patent No.: US 6,319,898 B1
(45) Date of Patent: *Nov. 20, 2001

(54) METHOD FOR INHIBITING EUKARYOTIC PROTEIN KINASES

(75) Inventors: Julian E. Davies, Vancouver; Barbara Waters, Delta; Geeta Saxena, Vancouver, all of (CA)

(73) Assignee: Terragen Diversity, Inc., Vancouver (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/174,263

(22) Filed: Oct. 16, 1998

Related U.S. Application Data

(60) Provisional application No. 60/062,515, filed on Oct. 17, 1997.

(51) Int. Cl.[7] .......................... A61K 38/02; A61K 38/12; C12Q 1/02; C12Q 1/48
(52) U.S. Cl. ................ 514/11; 435/15; 435/29; 514/2
(58) Field of Search .................. 514/2, 7, 8, 9, 514/11; 530/300, 317, 322, 323, 332; 435/15.29

(56) References Cited

U.S. PATENT DOCUMENTS

| 5,143,839 | 9/1992 | Blumberg et al. | 435/220 |
| 5,169,862 | * 12/1992 | Burke, Jr. et al. | 514/450 |
| 5,451,518 | 9/1995 | Kolesnick | 435/194 |
| 5,770,392 | 6/1998 | Davies et al. | 435/15 |

OTHER PUBLICATIONS

Laycock et al. Viscosin, A Potent Peptidolipid Biosurfactant . . . J. Agric. Food Chem. vol. 39, No. 3, pp. 483–489, 1991.*

Loing et al., Assessing Delivery of Lipopeptides into the Cytoplasm . . . Peptide Research. vol. 9, No. 5, pp. 229–232, 1996.*

Av–Gay, Y. and Davies, J. 1997 Components of eukaryotic–like protein signaling pathways in *Mycobacterium tuberculosis*. Microbial & Comparative Genomics 2:63–73.

Georgiou, G, Lin, S–C.,and Sharma, M. 1992 Surface–active compounds from microorganisms. Biotechnology 10:60–65.

Gerrard, J., Lloyd, R., Barsby, T., Haden, P., Kelly, M and Anderson, R. 1997 Massotolides A–H, antimycobacterial cyclic depsipeptides produced by two Pseudomonads isolated from marine habitats. J. Nat. Prod. 60:223–229.

Lauterwein, M., Oethinger, M., Belsner, K., Peters, T. and Marrc, R. 1995 In vitro activities of the lichen secondary metabolites vulpinic acid, (+)–usnic acid and (31)–usnic acid against aerobic and anaerobic microorganisms. Antimicrobial Agents and Chemotherapy 39:2541–2543.

(List continued on next page.)

Primary Examiner—Jeffrey E. Russel
(74) Attorney, Agent, or Firm—Pennie & Edmonds LLP

(57) ABSTRACT

A number of bacterial cultures were screened for the ability to inhibit sporulation using a strain Streptomyces 85E. Evaluations of the cultures which tested positive in this assay led to the discovery that lipopeptide biosurfactants such as surfactin and viscosin are effective inhibitors of eukaryotic protein kinase activity. Thus, a method for inhibiting eukaryotic protein kinase activity present in a sample or organism includes the step of adding to the sample or organism an effective inhibitory amount of a lipopeptide biosurfactant.

8 Claims, 1 Drawing Sheet

$$D-CH_3(CH_2)_6CHCH_2CO-L-Leu-D-Glu$$

VISCOSIN
$C_{54}H_{95}N_9O_{16}$ (1126)

OTHER PUBLICATIONS

Stachelhaus, T., Schneider, A. and Marahiel, M. 1996 Engineered biosynthesis of peptide antibiotics. Biochemical Pharmacology 52:177–186.

Toraya, T., Maoka, T., Tsuji, H. and Kobayashi, M. 1995 Purification and structural determination of an inhibitor of starfish ocytc maturation from a Bacillus species. Applied and Environmental Micro. 5:1799–1804.

Natsume et al. Calcium Signal Modulators Inhibit *Aerila mycelium* Formation in *Streptomyces alboniger*' , J. Antibiotics 45: 1026–1028 (1992).

Hong et al., "Effects of protein kinase inhibitors on in vitroprotein phosphorylation and cellular differentiation of *Streptomyces griseus*", Mol. Gen. Genetics 236: 347–354 (1993).

Kennelly et al., "Fancy Meeting You Here! A Fresh Look at 'Prokaryotic' Protein Phosphorylation", J. Bacteriol. 178: 4759–4764 (1996).

Karin et al., "Transcriptional control by protein phosphorylation: signal transmission from cell surface to nucleus", *Current Biology* 5: 747–757 (1995).

Ray, L.B., "Signals and Communiction," *Science* 268: 183 (1995).

Casey, P.J., "Protein Lipidation in Cell Signaling", *Science* 268: 224–225 (1995).

Burbulys et al., "Initiation of Sporulation in B. subtilis Is controlled by a Multicomponent Phosphrelay" *Cell* 64: 545–552 (1991).

Stock et al., "Protein Phosphorylation and Regulation of Adaptive Responses in Bacteria", *Micriobiol. Reviews* 53: 450–490 (1989).

South et al., "Tyrosine Kinase sctivity in *Pseudomonas aeruginosa*", *Molecular Microbiol.* 12: 903–910 (1994).

Chow et al., "Protein tyrosine phosphorylation in *Mycobacterijm tuberculosis*", *FEMS Microbiol. Lett.* 124: 203–208 (1994).

Li et al., "Cloning, Purification and Properties of a Phosphotyrosine Protein Phosphatase from *Streptomyces coelicolor* A3(2)", *J. Bactoeriol.* 178: 136–142 (1996).

Frasch et al., "Tyrosine Kinase in *Myxococcus xanthus*, a Multicellular Prokaryote", preprint of article submitted to *J. Bacteriol* (1996).

Zhang, C–C., "Bacterial Signalling Involving Eukaryotic–type Protein Kinases" *Molecular Microbiol.* 20: 91–5 (1996).

Zhang et al., "Identification of a Putative Eukaryotic–Like Protein Kinase Family in the Developmental Bacterium *Myxococcus xanthus*" *J. Bacteriol.* 174: 5450–5453 (1992).

Meydan et al., "Inhibition of acute lymphoblastic leukaemia by a Jak–2 inhibitor" *Nature* 379: 645–648 (1996).

"Leukemia–fighting drug found to work in mice", *Vancouver Sun*, Feb. 15, 1996, p. A11.

Clark et al., "Integrins and Signal Transduction: The Road Taken", *Science* 268: 233–234 (1995).

Machly–Rosen, D., "Localization of Protein Kinases by Anchoring Proteins: A Theme in Signal Transduction", *Science* 268: (1995).

De Franco et al., "Tyrosine Phosphatases and Antibody Response" *Science* 268: 263–264 (1995).

Levitzki, A. and A. Gazit, "Tyrosine Kinase Inhibition: An Approach to Drug Development", Science 267:1782–1788, Mar. 24, 1995.

Waters, B., et al., "Protein tyrosine phosphorylation in streptomycetes", FEMS Microbiology Letters 120:187–190, 1994.

House et al. (1987) "Protein Kinase C Contains a Pseudosubstrate Prototype in Its Regulatory Domain," *Science* 238: 1726–28.

Smith et al. (1990)"Specificities of Autoinhibitory Domain Peptides for Four Protein Kinases," *J. Biol. Chem.*, 265: 1837–40.

U.S. application No. 09/688,545, Davies et al., filed Oct. 16, 2000.

* cited by examiner

SEQUENCE LISTING

<160> NUMBER OF SEQ ID NOS: 3

<210> SEQ ID NO 1
<211> LENGTH: 7
<212> TYPE: PRT
<213> ORGANISM: Streptomyces

<400> SEQUENCE: 1

-continued

```
Glu Leu Leu Val Asp Leu Leu
 1               5

<210> SEQ ID NO 2
<211> LENGTH: 17
<212> TYPE: PRT
<213> ORGANISM: Artificial Sequence
<220> FEATURE:
<223> OTHER INFORMATION: Biotinylated peptide substrate
<220> FEATURE:
<221> NAME/KEY: SITE
<222> LOCATION: (1)
<223> OTHER INFORMATION: Xaa=Biotin-Glu

<400> SEQUENCE: 2

Xaa Gly Pro Trp Leu Glu Glu Glu Glu Ala Tyr Gly Trp Met Asp
 1               5                  10                  15

Phe

<210> SEQ ID NO 3
<211> LENGTH: 4
<212> TYPE: PRT
<213> ORGANISM: Artificial Sequence
<220> FEATURE:
<223> OTHER INFORMATION: Chromogenic substrate
<220> FEATURE:
<221> NAME/KEY: SITE
<222> LOCATION: (1)
<223> OTHER INFORMATION: Xaa=N-succinyl-Ala
<220> FEATURE:
<221> NAME/KEY: SITE
<222> LOCATION: (4)
<223> OTHER INFORMATION: Xaa=Phe-p-nitroanilide

<400> SEQUENCE: 3

Xaa Ala Pro Xaa
```

US 6,319,898 B1

METHOD FOR INHIBITING EUKARYOTIC PROTEIN KINASES

This application is a regular application filed under 35 USC §111(a) claiming priority from U.S. Provisional Application Ser. No. 60/062,515 filed Oct. 17, 1997.

BACKGROUND OF THE INVENTION

This application relates to a method for inhibiting eukaryotic protein kinases using lipopeptide biosurfactant compounds such as surfactin or viscosin.

Kinase and phosphatase enzymes play important roles in the regulation of both eukaryotic and prokaryotic cells. For example, in eukaryotic cells, the control of proliferation and differentiation is achieved by multiple signal transduction pathways that are regulated by the coordinated action of protein kinases and phosphatases.

Kinase activity in eukaryotes can be classified as one of three types: those enzymes which phosphorylate tyrosine residues; those which are specific for serine or threonine residues; and those which have dual specificity for both tyrosine and serine/threonine residues. Because of the importance of these enzymes in eukaryotic regulatory processes, it would be highly desirable to be able to inhibit kinases of the various classes selectively to assist in the elucidation of kinase and phosphatase mediated pathways, particularly those that may be of medical significance. In addition, selective kinase or phosphatase inhibitors have potential uses as therapeutics. For example, it has been reported that a tyrosine kinase blocker designated AG-940 specifically inhibits the Jak-2 protein tyrosine kinase which is deregulated and constitutively activated in the leukemic cells of acute lymphoblastic leukemia (ALL) patients. Meydan, et al. "Inhibition of acute lymphoblastic leukaemia by a Jak-2 inhibitor", *Nature* 379: 645–648 (1996). This inhibition induced changes in cells consistent with entry into apoptosis when tested in vitro. Further, the intravenous administration of the inhibitor into mice previously injected with ALL cells has been shown to be effective to eradicate the ALL cells from the marrow.

Notwithstanding the potential uses of kinase and phosphatase inhibitors, the number of known and characterized inhibitors is quite small. Staurosporine and K-252a are known to act as generalized kinase inhibitors, while herbimycin and radicol specifically inhibit tyrosine kinases, albeit with fairly low effectiveness. There are few if any known specific inhibitors for the MAP kinase family, an important group of enzymes thought to be central in the transmission of a wide variety of signals received at the cellular membrane to the transcriptional and replication machinery of the nucleus.

To facilitate the identification of new kinase and phosphatase inhibitors, we have developed an assay which is described in our prior U.S. Pat. No. 5,770,392, issued Jun. 23, 1998, and PCT Publication No. WO98/17822 claiming priority therefrom, which are incorporated herein by reference.

The assay offers a simple and effective pre-screening tool which is easily stored, and which lends itself to automated, high-throughput screening. Further, materials selected for further evaluation as a result of the assay are already known to be effective in the cell, unlike activities based on in vitro assay systems. Most importantly, the assay system is not affected by compounds in the materials being tested that are cytotoxic to mammalian cells, thus interfering with assays using mammalian cells, and avoids problems with protease contaminants that do not interfere with microbial morphological assays but are a serious problem with animal cell and isolated receptor assays.

This assay basically involves the steps of:
- adding the material to be tested for kinase inhibitory activity to a growing culture of a prokaryotic organism such as a streptomycete;
- allowing the culture to grow for a period of time in the presence of the material; and
- observing the culture for altered development relative to development of the prokaryotic organism grown in the absence of the material. Observation of altered development is indicative that the material has activity as an inhibitor of post-translational protein phosphorylation. In particular, the material to be tested can be added to a growing culture of the prokaryotic organism by placing a carrier disk bearing the material on a freshly seeded plate. Inhibition of the development of aerial mycelia and spore formation is an indicator that the material has activity as an inhibitor of post-translational protein phosphorylation.

SUMMARY OF THE INVENTION

Using the assay method of our prior invention, we have screened a number of bacterial cultures for the ability to inhibit sporulation of our preferred tester strain Streptomyces 85E. Evaluations of the cultures which tested positive in this assay have led to the discovery that lipopeptide biosurfactants such as surfactin and viscosin are effective inhibitors of eukaryotic protein kinase activity. Thus, the present invention provides a method for inhibiting eukaryotic protein kinase activity present in a sample or organism comprising the step of adding to the sample or organism an effective inhibitory amount of a lipopeptide biosurfactant.

BRIEF DESCRIPTION OF THE FIGURES

FIG. 1B is SEQ ID NO: 1.

DETAILED DESCRIPTION OF THE INVENTION

Figure 1A:
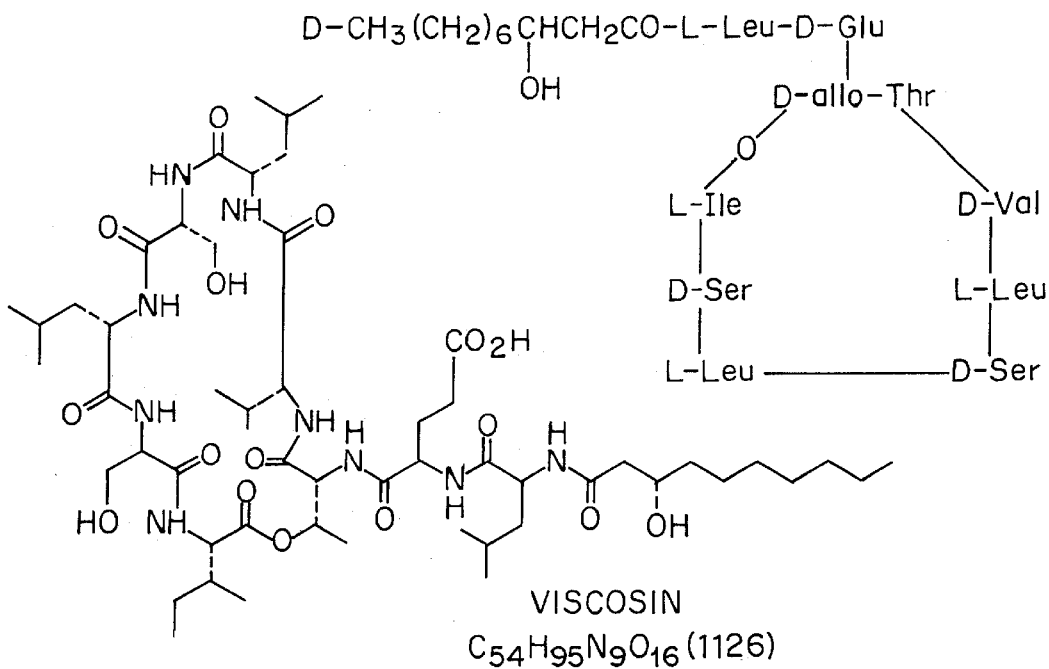
FIGS. 1A and 1B show the structures of viscosin and surfactin

Although eukaryotic and prokaryotic protein kinases generally have different substrate specificities, it has been observed that in some prokaryotic organisms eukaryote-like kinase and phosphatase activities may complement the two component systems typical of bacteria. In particular, streptomycetes, (Waters et al., "Protein tyrosine phosphorylation in streptomycetes", *FEMS Microbiology Letter* 120: 187–190 (1994); Li et al, "Cloning purification and properties of a phosphotyrosine protein phosphatase from *Streptomyces coelicolor* A3(2)", *J. Bact.* 178: 136–142 (1996)); *Myxococcus xanthus* (Zhang et al., "Identification of a putative eukaryotic-like protein kinase family in the developmental bacterium *Myxococcus xanthus*", *J. Bact.* 174: 5450–5453 9192); and cyanobacterial species. (Zhang, C-C, "Bacterial signaling involving eukaryotic-type protein kinases", *Molec. Microbiol.* 20: 9–15 (1996)). Because of this, certain microbes can be used to provide an assay for screening materials for activity as inhibitors of eukaryotic post-translational protein phosphorylation, and in particular for protein kinase activity.

We have used a wild strain of Streptomyces isolated from soil and designated Streptomyces WEC478-85E (hereinafter strain 85E) to test culture supernatants from various materials. Strain 85E has been deposited with the American Type Culture Collection in accordance with the provisions of the Budapest treaty and has been assigned Accession Number ATCC 55824.

In the test assay, material to be tested was applied to a filter paper disk and then placed on a plate which has been freshly seeded with the strain 85E test organism. The test organism is then allowed to grow in the presence of the filter paper disk for a period of 24 to 36 hours, after which the organism is evaluated for altered development in the zone around the disk. An observation of an inhibition of the formation of aerial mycelia and spores, without inhibition of the growth of vegetative mycelia is particularly indicative of the presence of an inhibitor of post-translational phosphorylation.

Once microbial cultures are identified which produce inhibitors of the type detected using the assay of the invention, the specific inhibitor that is produced by the culture were isolated and characterized. In particular, two bacterial cultures, WEC64-11C and WEC297-60A, which have been identified as strains of Pseudomonas and Bacillus, respectively, produce cell free supernatants which inhibit sporulation and formulation of aerial mycelia in tester strain 85E and other strains of Streptomyces. For each culture, an ethyl acetate extract was prepared by separately extracting the supernatant and the cells and combining the resulting products and this extract was fractionated on a silica gel column. Activity in the fractions recovered from the column was assayed to permit identification of an active inhibitory fraction. This fraction was further purified by chromatography, and the inhibitory compound was analyzed by mass spectroscopy.

Figure 1B:
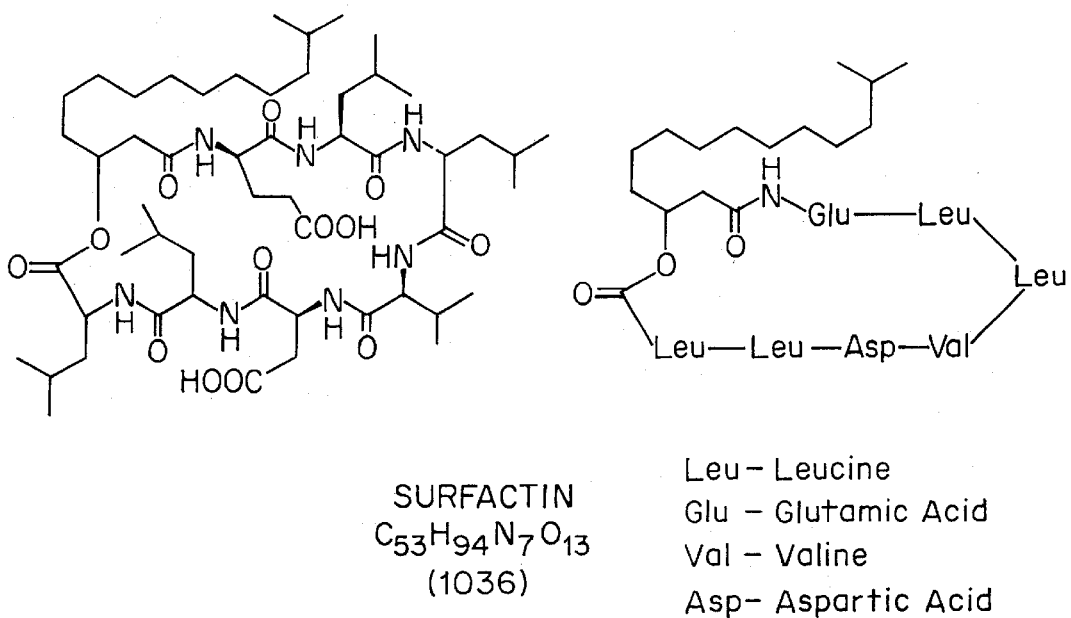

In the case of the Pseudomonas 11C, the product was determined to be viscosin. In the case of Bacillus 60A, the product was determined to be surfactin. The structures of viscosin and surfactin are shown in FIGS. 1A and 1B. Both are lipopeptide biosurfactants which are synthesized non-ribosomally by multi-functional peptide synthetases. (Stachelhaus et al., *Biochemical Pharmacology* 52: 177–186 (1996). Tests using pure viscosin and surfactin obtained from third-party sources confirmed the ability of these compounds to act as inhibitors of human c-Src kinase, a tyrosine kinase and to a lesser extent as inhibitors of the phosholipid dependent serine-threonine kinase, Protein Kinase C (PKC).

Surfactin and viscosin are best known for their ability to partition preferentially at interfaces; that is, both are surface-active compounds classed as biosurfactants. *Bacillus subtilis* and *Bacillus licheniformis* are well characterized producers of surfactin while *Pseudomonas fluorescens* is a known producer of viscosin. Both of these biosurfactants are lipopeptides known to have antibiotic properties which are probably related to their membrane acting characteristics. (review: Georgiou et al., *Biotechnology* 10: 60–65. (1992)). This same activity contributes to lysis of erythrocytes by surfactin. In a screen which was designed to detect compounds acting on hormonal signal transduction or cell-cycle regulation, bacterial culture supernatants were screened for their ability to inhibit maturation of starfish oocytes (Toraya et al., *Applied and Environmental Micro.* 5:1799–1804 (1995)). A positive result was obtained from a supernatant from a Bacillus species and following purification the active compound was identified as surfactin. The biochemical basis for the inhibition of oocyte maturation by surfactin has not yet been determined and these authors make no suggestions or claims that surfactin may be acting as a kinase inhibitor. It should be noted, however, that it is possible that a kinase-inhibition activity may be responsible for the maturation inhibition process since this developmental process, like sporulation, is regulated by kinase-mediated signaling cascades.

The present invention provides recognition of a new class of compounds, lipopeptide biosurfactants, which may be used as inhibitors of eukaryotic protein kinases for investigational and therapeutic purposes. While the invention is exemplified through two specific lipopeptide biosurfactants, namely the cyclic depsipeptides surfactin and viscosin, other lipopeptides might also be employed including serrawettin and depsidomycin. Depsidomycin is a compound which has been described as having immunomudulating activity (*J. Antibiotics* 43: 1195–1198 (1990) and which has been isolated from a strain identified in the screening test which has been tentatively identified based on rDNA sequence analysis as *Streptomyces lavendulae*.

The invention will now be further described and illustrated by way of the following, non-limiting examples.

EXAMPLE 1

For isolation of the active inhibitor from the supernatant of Bacillus 60A, a 3 liter culture of Bacillus 60A was grown in TSB (tryptic soy broth, Difco) for 24 hours at 30° C. from a 1% v/v inoculum from a freshly grown seed culture. Cells were harvested by centrifugation at 7880×g and both the supernatant and cell pellet were extracted separately with 3 volumes of ethyl acetate and 3 volumes of 20% methanol in ethyl acetate, respectively. The crude ethyl acetate extracts were fractionated on a low mesh silica gel column in an increasing methanol gradient in chloroform. Inhibitory activity in the fractions was monitored by thin layer chromatography of aliquots on silica gel. Following development in chloroform:methanol (95:5 v/v) plates were transferred to square culture dishes and overlaid with ISP (Difco) soft agar (0.6%) containing an inoculum of $10^7$–$10^8$ cfu from a fresh culture of Streptomyces 85E. After incubation at 30° C. for 24 to 30 hours fractions with activity could be identified by inhibition of sporulation in a zone over one or more spots. Using this method an active fraction eluting at 12% methanol in chloroform was identified and further purified by column chromatography on Sephadex LH-20 in chloroform:methanol (1:1 v/v). Once again the active fraction was identified and chromatographed once more on Sephadex LH-20, this time in chloroform:methanol 8:2 v/v. 44.2 mg of a pure, active compound designated TDI-4 were recovered. TDI-4 is a white powder, soluble in chloroform, which develops as a pink spot when sprayed with vanillin-$H_2SO_4$ following TLC in chloroform: methanol: acetone, 4:3:3 v/v. At this stage it was subjected to low resolution FAB-mass spectroscopy which gave $M^+$ at m/z 1036. High resolution FAB-MS suggested the formula $C_{53}H_{93}N_7O_{13}$. Given the source of this compound, its molecular weight and probable formula an identification as the peptide surfactin seemed likely. Amino acid analysis yielded a composition of leucine×4, aspartic acid×1, glutamic acid×1 and valine×1, a composition consistent with surfactin. TDI-4 was then directly compared to surfactin from *Bacillus subtilis* (obtained from Sigma, molecular weight 1036) by co-TLC and by NMR spectroscopy and was found to match.

EXAMPLE 2

For isolation of the active inhibitor from Pseudomonas 11C, a 10 liter culture of Pseudomonas 11C was grown in tryptic soy broth for 24 hours at 30° C. from a 1% v/v inoculum from a freshly grown seed culture. Cells were harvested by centrifugation at 7880×g and both the supernatant and cell pellet were extracted separately with ethyl acetate and 20% methanol in ethyl acetate, respectively. As before, the crude ethyl extracts were fractionated initially on a silica gel column in chloroform, followed by further chromatography of active fractions (identified by TLC and an overlay bioassay as described previously) on Sephadex LH-20 in methanol. 4.2 mg of a pure active compound designated TDI-5 were recovered. TDI-5 is a yellowish white compound which also develops as a pink spot on a TLC plate when developed in chloroform:methanol:acetone (6:2:2) and sprayed with vanillin-$H_2SO_4$. The LRFAB-MS analysis suggested a molecular weight of 1126. The molecular formula for m/z 1126 was determined to be $C_{54}H_{96}N_9O_{16}$ by HRFAB-MS analysis. Based on this information and the source of the compound, an identification as the peptide viscosin seemed likely and amino acid analysis yielded a composition of leucine×3., valine×1, serine×2, isoleucine×1 and glutamic acid×1. The presence of a ninth amino acid as D-allo-threonine was demonstrated by the mass fragmentation data calculated from LRFAB-MS. TDI-5 was then compared to an authentic sample of viscosin (a gift from Raymond Anderson) by co-TLC and found to match.

EXAMPLE 3

Testing the purified surfactin and viscosin was carried out to determine a) their ability to inhibit sporulation of Streptomyces species and b) their ability to inhibit the activity of eukaryotic protein kinases.

a) Inhibition of Sporulation

Samples of surfactin prepared as described from Bacillus 60A as well as surfactin from *Bacillus subtilis* with the same molecular weight (1036) obtained from Sigma were tested for their ability to inhibit sporulation of Streptomyces 85E.

| Amount of surfactin applied to the disc | Diameter of zone of inhibition of sporulation |
|---|---|
| 1 ug, Sigma surfactin | 12 mm |
| 5 ug, Sigma surfactin | 15 mm |
| 10 ug, Sigma surfactin | 20 mm |
| 1 ug surfactin from Bacillus 60A | 13 mm |
| 5 ug surfactin from Bacillus 60A | 17 mm |
| 10 ug surfactin from Bacillus 60A | 19 mm |

Surfactin in these concentrations does not inhibit growth of the vegetative mycelia but inhibits development of aerial mycelia and spore formation. The effect is very persistant, lasting for at least 3 to 4 days after unaffected portions of the culture have sporulated. Eventually the inhibition is overcome and the culture sporulates. It has also been noted that surfactin in these concentrations does not inhibit growth of other bacterial species such as *E. coli* or *S. aureus*. However, surfactin has been reported to have anti-mycobacterial activity (Stachelhaus et al., 1996) and this has been confirmed with tests of these samples on *Mycobacterium phlei*. (25 ug Sigma surfactin applied to a disc produced a 12 mm zone of growth inhibition and 20 ug of surfactin from Bacillus 60A produced an 8 mm zone of growth inhibition.) The mechanism of this inhibition is not known; however, Mycobacteria have also been shown to possess certain elements of eukaryotic signal transduction pathways (Av-Gay and Davies, 1997) and it is possible that surfactin, acting as a kinase inhibitor, is interfering with signaling processes in this organism. It is further possible that the screen described which potentially detects inhibitors of eukayotic signaling processes may also have potential in the discovery of novel antimycobacterial agents. At least 8 cell-free supernatants which were found to inhibit sporulation of Streptomyces 85E also have antimycobacterial activity in tests of inhibition of *M. aurum, M. phlei* and *M. tuberculosis* but do not inhibit growth of *S. aureus* or *E. coli*. These active supernatants are from two species of Streptomyces, a Bacillus species and a Pseudomonas species isolated from soils. The active compounds from the Streptomyces sp. have not yet been purified and identified. The Bacillus species are related to 60A and are probably producing surfactin while the Pseudomonad is a viscosin producer.

Viscosin purified from Pseudomonas 11C was also shown to inhibit sporulation of Streptomyces 85E (15 ug produces a 30 mm zone of persistent sporulation inhibition with no inhibition of growth of vegetative mycelia). Viscosin has also been reported to have antimycobacterial activity (Gerared et al., 1997) and this was confirmed with inhibition of growth of *M. aurum*. (25 ug applied to a disc resulted in a 9 mm zone of growth inhibition.)

b) Inhibition of Eukaryotic Protein Kinases

I) Inhibition of the Protein Tyrosine Kinase c-Src

Human c-Src ($p60^{c-src}$) was obtained from Upstate Biotechnology. The activity of the enzyme was assayed in an ELISA based assay developed by Pierce. Following their protocol, 500 ng of a biotinylated peptide substrate in distilled water (Pierce biotinylated peptide substrate #2, sequence Biotin-EGPWLEEEEEAYGWMDF) (SEQ ID NO:2) was added to a NeutrAvidin™ coated well, incubated at 37° C. for 30 minutes to allow binding to the well then washed with Tris-buffered saline (TBS, 25 mM Tris, 0.15 M NaCl, pH 7.6). For each reaction, a reaction buffer mixture was prepared to contain 10 ul of src assay buffer (100 mM Tris-HCl, pH 7.2, 25 mM $MnCl_2$, 2.0 mM EGTA, 0.25 mM $Na_3VO_4$, 125 mM Mg Acetate) 20 ul of ATP/$MgCl_2$ buffer (5 mM ATP, 50 MM $MgCl_2$ in TBS) and 1 ul of protease inhibitor mix (PMSF and pepstatin, final concentrations in Rx: 0.5 mM and 1.5 uM). The src enzyme is supplied at a concentration of 3 units per microliter and dilutions of the kinase were prepared in 1% bovine serum albumin (BSA) in TBS typically to final concentrations of 0.2 or 0.4 units in 10 ul. 10 ul of a solution of a compound to be tested for inhibitory activity was added to the reaction buffer mixture and allowed to stand 10–15 min. at room temperature, then 10 ul of the diluted kinase enzyme was added and the mixture was allowed to stand 10 min. at room temperature before addition to the substrate coated well. The plate was incubated at 30° C. for varying periods of time then the contents were washed out with repeated rinsings with TBS. A mouse monoclonal anti-phosphotyrosine antibody (PY20) conjugated to horseradish peroxidase (Pierce) was diluted 1:2000 in 1% BSA diluent from 1 mg/ml and 75 ul of this dilution was added to each well, incubated 1 hour at 37° C. then washed out with repeated rinsings with TBS.

100 ul of horseradish peroxidase substrate solution (3,3', 5,5' tetramethylbenzidine and $H_2O_2$, Pierce TMB-ELISA) was added to each well and after 10 min. the reaction was stopped with the addition of 100 ul of 1 N $H_2SO_4$. Absorbance was read at 450 nm in a Molecular Devices V-max plate reader.

Examples of inhibition detected using this assay: (Values reported are the absorbance readings after subtraction of a blank well containing no enzyme.)

I. Human c-Src Kinase Incubated 30 Min. at 30° C. with 10 ug of Surfactin (srf) or 5 ug of Viscosin (Vis)

| Control reactions | Reactions with surfactin | Reactions with viscosin |
| --- | --- | --- |
| 0.05 unit c-Src 0.315 | 0.05 unit c-Src + 10 ug srf 0.050 | |
| 0.1 unit c-Src 0.391 | 0.1 unit c-Src + 10 ug srf 0.093 | 0.1 unit c-Src + 5 ug vis 0.186 |
| 0.2 unit c-Src 0.396 | 0.2 unit c-Src + 10 ug srf 0.191 | 0.2 unit c-Src + 5 ug vis 0.175 |
| 0.4 unit c-Src 0.517 | 0.4 unit c-Src + 10 ug srf 0.311 | 0.2 unit + 5 ug vis 0.251 |

II. Human c-Src kinase incubated 5 min. at 30° C. with surfactin or viscosin:

| Control | | |
| --- | --- | --- |
| 0.2 unit c-Src 0.220 | 0.2 unit c-Src + 10 ug srf 0.087 | 0.2 unit c-src + 5 ug vis 0.123 |
| | 0.2 unit c-Src + 5 ug srf 0.185 | 0.2 unit c-Src + 2.5 ug vis 0.210 |

10 ug of surfactin added to these reactions represents a concentration of 200 uM in the reaction and this concentration as well as 100 uM has inhibited the activity of the tyrosine kinase tested. Similarly viscosin at a concentration of 90 uM has inhibited the activity of this kinase. The preparations of the inhibitors from the soil bacterial isolates as well as the Sigma preparation of surfactin have been tested for residual protease activities by various methods including:

a. incubation with the chromogenic substrate N-succinyl-ala-ala-pro-phe p-nitroanilide (SEQ ID NO.3.)

b. incubation with a mixture of proteins followed by SDS-PAGE analysis c. zymogram analysis in a gel containing gelatin as the protease substrate The crude culture supernatant from the Bacillus clearly contains protease activity but none was detectable in the purified preparations of surfactin. The Pseudomonas culture supernatant contains a lesser amount of protease activity and again none was detected in the purified preparation of viscosin. Both of these compounds are surfactants and the possibility that the apparent inhibition was due to interference with either the avidin-biotin interaction or the adherence of the avidin to the wells was tested by preincubating the substrate coated well with a reaction mixture containing surfactin or viscosin but no enzyme for 30 minutes. The well was then washed with repeated rinsings of TBS and a standard kinase reaction without the inhibitors was set up. This reaction showed no decrease in activity compared to a control reaction. Thus, it is concluded that surfactin and viscosin are inhibitors of this tyrosine kinase.

ii) Inhibition of the Phospho-lipid Dependent Serine-threonine Kinase Protein Kinase C (PKC)

Protein Kinase C purified from rat brain was obtained from Upstate Biotechnology. The activity of the enzyme was assayed in a colorimetric assay developed by Pierce. Reaction mixtures were prepared to contain 5 ul each of the 5×reaction buffer, the dye labeled glycogen synthase synthetic peptide substrate reconstituted to 1.77 mM and the 5× activator solution of phosphatidyl-L-serine, all supplied by Pierce in a PKC assay kit. The activator solution was sonicated for 30 sec. on ice prior to use. 1 ul of the kinase (equivalent to 10 ng of enzyme with a specific activity of 12.1 units/mg) was added to 10 ul of a solution containing the compound to be tested for inhibitory activity and allowed to stand at room temperature for 10 minutes then transferred to the reaction tube containing the substrate and incubated 30 min. at 30° C. After incubation 20 ul of each sample was applied to the centre of the affinity membrane in the separation units supplied with the assay kit. These membranes specifically bind the phosphorylated dye labeled substrate while non-phosphorylated peptide will pass through when spun at low speeds. After washing the membranes the phosphorylated peptide was eluted by spinning with the elution buffer and absorbance read at 570 nm in a Molecular Devices V-max plate reader.

Viscosin at a concentration of 200 uM in the reaction was not inhibitory. Surfactin at a concentration of 380 uM in the reaction was only minimally inhibitory as shown in the following example:

| Control reaction | |
| --- | --- |
| 10 ng PKC 0.228 | 10 ng PKC + 10 ug srf 0.181 |

Polymyxin B is a peptide with a molecular weight similar to viscosin and surfactin and is a recognized inhibitor of PKC. Inhibition of the kinase could be detected in this assay system as shown by the following example:

| Control reaction | |
| --- | --- |
| 10 ng PKC 0.203 | 10 ng PKC + 10 ug polymyxin B 0.035 |

Thus it was concluded that surfactin and viscosin are more potent inhibitors of the tyrosine kinase tested than this serine-threonine kinase.

We claim:

1. A method for inhibiting a mammalian protein kinase present in a sample or organism comprising the step of adding to the sample or organism an effective inhibitory amount of a lipopeptide biosurfactant, wherein the lipopeptide biosurfactant inhibits sporulation of Streptomyces.

2. The method of claim 1, wherein the lipopeptide biosurfactant is a cyclic depsipeptide.

3. The method of claim 2, wherein the lipopeptide biosurfactant is surfactin.

4. The method of claim 2, wherein the lipopeptide biosurfactant is viscosin.

5. The method of claim 1 wherein the mammalian protein kinase is a human protein kinase.

6. The method of claim 1 wherein the mammalian protein kinase is a tyrosine protein kinase.

7. The method of claim 1 wherein the mammalian protein kinase is a serine-threonine protein kinase.

8. The method of claim 1, 2, 3, 4, 5, 6, or 7, wherein the lipopeptide biosurfactant is purified.

* * * * *